United States Patent [19]
Bhatnagar

[11] Patent Number: 5,652,219
[45] Date of Patent: Jul. 29, 1997

[54] HEMOREGULATORY PEPTIDES

[75] Inventor: Pradip Kumar Bhatnagar, Exton, Pa.

[73] Assignee: SmithKline Beecham Corporation, Philadelphia, Pa.

[21] Appl. No.: 624,616

[22] PCT Filed: Oct. 28, 1994

[86] PCT No.: PCT/US94/12421

§ 371 Date: Apr. 12, 1996

§ 102(e) Date: Apr. 12, 1996

[87] PCT Pub. No.: WO95/11693

PCT Pub. Date: May 4, 1995

[51] Int. Cl.[6] .............. C07K 5/00; C07K 7/00; C07K 17/00; A61K 38/00

[52] U.S. Cl. .............. 514/15; 514/16; 514/17; 530/328; 530/329; 530/330

[58] Field of Search .............. 530/328, 329, 530/330; 514/16, 17

[56] References Cited

U.S. PATENT DOCUMENTS 4,499,081   2/1985   Laerum ............... 530/330 X

OTHER PUBLICATIONS

Donald Metcalf, "The Granulocyte–Macrophage Colony Stimulating Factors", *Cell*, 43, pp. 5–6 (Nov., 1985).

*Primary Examiner*—Howard E. Schain
*Attorney, Agent, or Firm*—Linda E. Hall; Stephen A. Veneti; Edward T. Lentz

[57] ABSTRACT

The invention provides compounds of general formula (I). The compounds have hemoregulatory activities and can be used to stimulate haematopoiesis and for the prevention and treatment of viral, fungal and bacterial infectious diseases.

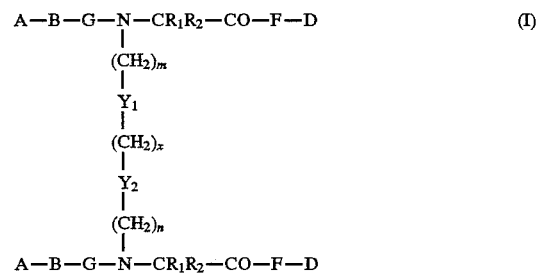

8 Claims, No Drawings

HEMOREGULATORY PEPTIDES

FIELD OF THE INVENTION

The present invention relates to novel compounds which have hemoregulatory activities and can be used to stimulate haematopoiesis and for the treatment of viral, fungal and bacterial infectious diseases.

BACKGROUND OF THE INVENTION

A variety of regulatory messengers and modifiers such as colony stimulating factors, interferons, and different types of peptides are responsible for the regulation of myelopoiesis. Metcalf, *Cell*, 43:5 (1985); Baserga R., Foa P., Metcalf D., Polli EE (eds), *Biological Regulation of Cell Proliferation* (1986); Nicola et al., *J. Cell Physiol.* 128:501 (1986), Zoumbos et al., *Proyr. Hemat.* 1:341 and 14:201 (1986); Werner et al., *Experientia* 42:521 (1986).

In 1982, a synthetic hemoregulatory pentapeptide was reported to have a selective inhibitory effect on myelopoietic cells both in vitro and in vivo, where the main effect seems to be on myelopoietic stem cells (CFU-gm), Paukovits et al., Z. Naturforsch 37:1297 (1982) and U.S. Pat. No. 4,499,081. This peptide is believed to be an analogue of a naturally occurring granulopoiesis inhibition factor which has been found in minute quantities in bone marrow extracts.

In 1987, Laerum et al., reported that the oxidation product of this peptide was a dimer (HP-5) formed by disulfide bridges. This dimer has the opposite effect of the monomer as it strongly stimulates colony formation of both human and murine CFU-gm in vitro and up-regulates murine myelopoietic cells in vivo. It is claimed in European Application No. 87309806.5

The dimer is reported as being useful in stimulating myelopoiesis in patients suffering from reduced myelopoietic activity, including bone marrow damage, agranulocytosis and aplastic anemia including patients having depressed bone marrow function due to immunosuppressive treatment to suppress tissue reactions i.e. in bone marrow transplant surgery. It may also be used to promote more rapid regeneration of bone marrow after cytostatic chemotherapy and radiation therapy for neoplastic and viral diseases. It may be of particular value where patients have serious infections due to a lack of immune response following bone marrow failure.

We have now found certain novel compounds which have a stimulative effect on myelopoietic cells and are useful in the treatment and prevention of viral, fungal and bacterial diseases.

SUMMARY OF THE INVENTION

This invention comprises compounds, hereinafter represented as Formula (I), which have hemoregulatory activities and can be used to stimulate haematopoiesis and in the prevention and treatment of bacterial, viral and fungal diseases.

These compounds are useful in the restoration of leukocytes in patients with lowered cell counts resulting from a variety of clinical situations, such as surgical induced myelosuppression, AIDS, ARDS, congenital myelodysplacis, bone marrow and organ transplants; in the protection of patients with leukopenia from infection; in the treatment of severely burned patients and in the amelioration of the myelosuppression observed with some cell-cycle specific antiviral agents and in the treatment of infections in patients who have had bone marrow transplants, especially those with graft versus host disease, in the treatment of tuberculosis and in the treatment of fevers of unknown origin in humans and animals. The compounds are also useful in the treatment and prevention of viral, fungal and bacterial infectious diseases, particularly Candida, Herpes and hepatitis in both immunosuppressed and "normal" subjects.

These compounds may also be used in combination with the monomers of co-pending U.S. application Ser. No. 07/799,465 and U.S. Pat. No. 4,499,081, incorporated by reference herein, to provide alternating peaks of high and low activity in the bone marrow cells, thus augmenting the natural circadian rhythm of haematopoiesis. In this way, cytostatic therapy can be given at periods of low bone marrow activity, thus reducing the risk of bone marrow damage, while regeneration will be promoted by the succeeding peak of activity. This invention is also a pharmaceutical composition, which comprises a compound of Formula (I) and a pharmaceutically acceptable carrier.

This invention further constitutes a method for stimulating the myelopoietic system of an animal, including humans, which comprises administering to an animal in need thereof, an effective amount of a compound of Formula (I).

This invention also constitutes a method for preventing and treating viral, fungal and bacterial infections in immunosuppressed and normal animals, including humans, which comprises administering to an animal in need thereof, an effective amount of a compound of Formula (I).

DETAILED DESCRIPTION OF THE INVENTION

1. A compound of the following formula:

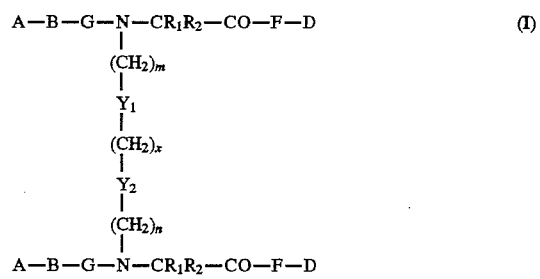

wherein:

$Y_1$ and $Y_2$ are independently $CH_2$ or S;

x is 0, 1, 2, 3, or 4;

m is 0 or 2;

n is 0 or 2;

A is pyroglutamic acid, proline, glutamine, tyrosine, glutamic acid, 2-thiophene carboxylic acid, picolinic acid, cyclohexane carboxylic acid, tetrahydro-2-furoic acid, tetrahydro-3-furoic acid, 2-oxo-4-thiazolidine carboxylic acid, cyclopentane carboxylic acid, 3-thiophene carboxylic acid, (S)-(+)-5-oxo-2-tetrahydrofuran carboxylic acid, pipecolinic acid, pyrrole carboxylic acid, isopyrrole carboxylic acid, pyrazole carboxylic acid, isoimidazole carboxylic acid, triazole carboxylic acid, dithiole carboxylic acid, oxathiole carboxylic acid, isoxazole carboxylic acid, oxazole carboxylic acid, thiazole carboxylic acid, isothiazole carboxylic acid, oxadiazole carboxylic acid, oxatriazole carboxylic acid, oxathiolene carboxylic acid, oxazine carboxylic acid, oxathiazole carboxylic acid, dioxazole carboxylic acid, pyran carboxylic acid, pyrimidine carboxylic acid, pyridine carboxylic acid, pyridazine carboxylic acid, pyrazine carboxylic acid, piperazine carboxylic acid, triazine carboxylic acid, isooxazine carboxylic acid, oxathiazene carboxylic acid, morpholine carboxylic acid, indole carboxylic acid, indolenene carboxylic acid, 2-isobenzazole carboxylic acid, nicotinic acid, isonicotinic acid, pyrazolo [3,4-b]pyrrole carboxylic acid, pyrazolo [3,4-b]pyrrole carboxylic acid, isoindazole carboxylic acid, indoxazine carboxylic acid, benzoxazole carboxylic acid, anthranil carboxylic acid, quinoline carboxylic acid, isoquinoline carboxylic acid, cinnoline carboxylic acid, quinazolene carboxylic acid, naphthyridine carboxylic acid, pyrido[3,4-b]-pyridine carboxylic acid, pyrido[3,2-b]-pyridine carboxylic acid, pyrido[4,3-b]pyridine carboxylic acid, 1,3,2-benzoxazine carboxylic acid, 1,4,2-benzoxazine carboxylic acid, 2,3,1-benzoxazine carboxylic acid, 3,1,4-benzoxazine carboxylic acid, 1,2-benzisoxazine carboxylic acid, 1,4-benzisoxazine carboxylic acid, carbazole carboxylic acid, acridine carboxylic acid, or purine carboxylic acid;

B is serine, threonine, glutamic acid, tyrosine, cysteine or aspartic acid;

G is glutamic acid, tyrosine, aspartic acid, serine, alanine, phenylalanine, histidine, isoleucine, leucine, methionine, threonine, trytophan, norleucine, allothreonine, glutamine, asparagine, valine, proline, glycine, lycine, β-alanine or sarcosine;

D is lysine, arginine, tyrosine, N-methylarginine, arginine, aspartic acid, ornithine, serine, alanine, phenylalanine, histidine, isoleucine, leucine, methionine, threonine, trytophan, norleucine, allothreonine, glutamine, asparagine, valine, proline, glycine, lysine, β-alanine, sarcosine, or diaminohexynoic acid; or the carboxyamide, or the hydroxy methyl or N-methyl derivative thereof;

F is tyrosine or a peptide bond;

$R_1$ and $R_2$ are independently hydrogen, $C_{1-3}$alkyl, $C_{2-4}$alkenyl, $C_{2-4}$alkynyl, $(CH_2)_nAr$ or $(CH_2)_xR_3$;

$R_3$ is OH, SH, $NH_2$, $-NH\,C(NH_2)NH$, $CO_2H$ or $CONH_2$;

Ar is phenyl, pyridyl, furyl, naphthyl, thiophenyl, pyrrolyl, imidazolyl, indolyl or hydroxyphenyl;

Provided that:
when $Y_1$ and $Y_2$ are S, x is 0, 2, 3 or 4 and m and n are 2; or
when $Y_1$ and $Y_2$ are $CH_2$, x is 0, 1, 2, 3 or 4 and m and n are 0; or
when $Y_1$ is S and $Y_2$ is $CH_2$, x is 0, m and n are 2;

or a pharmaceutically acceptable salt thereof.

All alkyl, alkenyl, alkynyl and alkoxy groups may be straight or branched.

The compounds of the present invention may contain one or more asymmetric carbon atoms and may exist in racemic and optically active form. All of these compounds and diastereoisomers are contemplated to be within the scope of the present invention.

Also included in this invention are pharmaceutically acceptable salt complexes of the compounds of this invention. It should be noted in formula (I) that A comprises the terminal amino group. Similarly, D comprises the terminal carboxyl group, or the carboxamide or hydroxy methyl derivative thereof.

The abbreviations and symbols commonly used in the art are used herein to described the peptides:
Ala=alanine
pGlu=pyroglutamic acid
Pro=proline
Glu=glutamic acid
Asp=aspartic acid
Tyr=tyrosine
Pic=picolinic acid
Ppc=pipecolinic acid
Gly=glycine
Orn=ornithine
Lys=lysine
Cys=cysteine
Ser=Serine In accordance with conventional representation, the amino terminus is on the left and the carboxy terminus is on the right. All chiral amino acids may be in the D or L absolute configuration. All optical isomers are contemplated.

The amino terminus may be protected by acylation. Examples of such protecting groups are, t-butoxycarbonyl (t-Boc), $CH_3CO$ and Ar—CO (Ar=benzyl, or phenyl).

The C-terminus may be carboxyl as in the case of the natural amino acid or the carboxamide $-C(O)NH_2$ or hydroxymethyl ($-CH_2-OH$) derivative.

Preferred compounds are those in which:

A is pyroglutamic acid, picolinic acid, proline, tyrosine, or pipecolinic acid;

B is glutamic acid, serine, aspartic acid or tyrosine;

G is aspartic acid, glutamic acid, tyrosine or lysine;

D is lysine, or the carboxyamide derivative thereof, arginine, N-methylarginine, 2,6-diamino-4-hexynoic acid, aspartic acid or ornithine;

$Y_1$ and $Y_2$ are $CH_2$;

x is 0 or 2;

m and n are 0.

More preferred are compounds wherein:

A is pyroglutamic acid, proline and picolinic acid;

B is glutamic acid, aspartic and or serine;

G is aspartic acid or glutamic acid;

D is lysine or the carboxyamide derivative thereof;

F is a bond;

$Y_1$ and $Y_2$ are $CH_2$; and x is 0 or 2 and the chiral amino acids are in the L absolute configuration.

The present invention provides compounds of Formula (I)

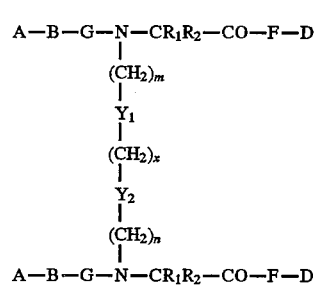

which can be prepared by a process which comprises:
(a) where x is 1, 2, 3 or 4; and $Y_1$, $Y_2$, m, n, $R_1$ and $R_2$ are defined as in Formula (I); reacting a compound of Formula (II):

$$H_2N—(CH_2)_m—Y_1—(CH_2)_x—Y_2—(CH_2)_n—NH_2 \quad (II)$$

with two equivalents of a compound of Formula (III)

$$Br—CR_1R_2—CO_2Et \quad (III)$$

in a suitable solvent such as $CH_2Cl_2$ to provide a compound of Formula (IV).

$$\begin{array}{l} NH—CR_1R_2—CO_2Et \\ | \\ (CH_2)_m \\ | \\ Y_1 \\ | \\ (CH_2)_x \\ | \\ Y_2 \\ | \\ (CH_2)_n \\ | \\ NH—CR_1R_2—CO_2Et \end{array} \quad (IV)$$

Compound (IV) is reacted with excess di-t-butyl dicarbonate in a suitable solvent such as $CH_2Cl_2$ to provide a compound of Formula (V):

$$\begin{array}{l} BOC—N—CR_1R_2—CO_2Et \\ | \\ (CH_2)_m \\ | \\ Y_1 \\ | \\ (CH_2)_x \\ | \\ Y_2 \\ | \\ (CH_2)_n \\ | \\ BOC—N—CR_1R_2—CO_2Et \end{array} \quad (V)$$

Compound (V) is reacted with aqueous base such as sodium hydroxide in a suitable solvent such as THF to hydrolyze the ethyl esters. This compound is subsequently coupled to a suitably protected peptide of Formula (VI):

$$F—D \quad (VI)$$

using standard coupling reagents such as EDC/HOBt in a suitable solvent such as N,N-dimethylformamide to provide a compound of Formula (VII):

$$\begin{array}{l} BOC—N—CR_1R_2—CO—F—D \\ | \\ (CH_2)_m \\ | \\ Y_1 \\ | \\ (CH_2)_x \\ | \\ Y_2 \\ | \\ (CH_2)_n \\ | \\ BOC—N—CR_1R_2—CO—F—D \end{array} \quad (VII)$$

The BOC protecting groups of Compound (VII) are then removed using a suitable reagent such as trifluoroacetic acid in a suitable solvent such as $CH_2Cl_2$. The resulting diamine is then sequentially coupled to suitably protected BOC-amino acids G, B and A using standard solution phase amino acid synthesis methods such as those found in M. Bodansky et al., "Peptide Synthesis", John Wiley and Sons, Inc., New York, N.Y. (1976) (incorporated herein by reference). Removal of the protecting groups with anhydrous hydrogen fluoride provides compounds of Formula (I).

b) where x is 0; and $Y_1$, $Y_2$, m, n, $R_1$ and $R_2$ are defined as in Formula (I); reacting a compound of Formula (VIII):

$$PY_1—(CH_2)_n—NH_2 \quad (VIII)$$

where P is a suitable protecting group such as benzyl; with one equivalent of a compound of Formula (III) in a suitable solvent such as $CH_2Cl_2$ to provide a compound of Formula (IX):

$$PY_1—(CH_2)_n—NH—CR_1R_2—CO_2Et \quad (IX)$$

Compound (IX) is reacted with excess di-t-butyl dicarbonate in a suitable solvent such as $CH_2Cl_2$ to provide a compound of Formula (X):

$$\begin{array}{l} BOCN—CR_1R_2—CO_2Et \\ | \\ (CH_2)_n \\ | \\ Y_1P \end{array} \quad (X)$$

The BOC protecting group of Compound (X) is then removed using a suitable reagent such as trifluoroacetic acid in a suitable solvent such as $CH_2Cl_2$. The resulting amine is sequentially coupled to suitably protected BOC-amino acids G, B and A using standard solution phase amino acid synthesis methods to provide a compound of Formula (XI):

$$\begin{array}{l} A—B—G—N—CR_1R_2—CO_2Et \\ | \\ (CH_2)_n \\ | \\ Y_1P \end{array} \quad (XI)$$

For compounds wherein $Y_1$ is S, removal of the protecting groups with anhydrous hydrogen fluoride and treating the resulting compound with an oxidizing agent such as glutathione in a suitable medium such as TRIS buffered at pH 8.5 provides compounds of Formula (I)

In general, in order to exert a stimulatory effect, the peptides of the invention may be administered to human patients by injection in the dose range of 0.5 ng to 1 mg preferably 5–500 ng, or orally in the dose range of 50 ng to 5 mg, for example 0.01 mg to 1 mg per 70 kg body weight per day; if administered by infusion or similar techniques, the dose may be in the range 0.005 ng to 1 mg per 70 kg body weight, for example about 0.03 ng over six days. In principle, it is desirable to produce a concentration of the peptide of about $10^{-15}M$ to $10^{-5}M$ in the extracellular fluid of the patient.

According to a still further feature of the present invention there are provided pharmaceutical compositions comprising as active ingredient one or more compounds of Formula (I) as herein before defined or physiologically compatible salts thereof, in association with a pharmaceutical carrier or excipient.

The compositions according to the invention may be presented for example, in a form suitable for oral, nasal, parenteral or rectal administration.

As used herein, the term "pharmaceutical" includes veterinary applications of the invention. These peptides may be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline and water. Solid carriers include starch, lactose, calcium sulfate dihydrate, terra alba, magnesium stearate or stearic acid, talc, pectin, acacia, agar or gelatin. The carrier may also include a sustained release material such a glyceryl monostearate or glyceryl distearate, alone or with a wax. The amount of solid carrier varies but, preferably will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. Capsules containing one or several active ingredients may be produced, for example, by mixing the active ingredients with inert carriers, such as lactose or sorbitol, and filling the mixture into gelatin capsules. When a liquid carrier is used, the preparation will be in the form of a syrup, elixir, emulsion or an aqueous or non-aqueous suspension. Such a liquid formulation may be administered directly p.o. or filled into a soft gelatin capsule. Organ specific carrier systems may also be used.

Alternately pharmaceutical compositions of the peptides of this invention, or derivatives thereof, may be formulated as solutions of lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration and contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

For rectal administration, a pulverized powder of the peptides of this invention may be combined with excipients such as cocoa butter, glycerin, gelatin or polyethylene glycols and molded into a suppository. The pulverized powders may also be compounded with an oily preparation, gel, cream or emulsion, buffered or unbuffered, and administered through a transdermal patch.

Nasal sprays may be formulated similarly in aqueous solution and packed into spray containers either with an aerosol propellant or provided with means for manual compression.

Dosage units containing the compounds of this invention preferably contain 0.1–100 mg, for example 1–50 mg of the peptide of formula (I) or salt thereof.

According to a still further feature of the present invention there is provided a method of inhibition of myelopoiesis which comprises administering an effective mount of a pharmaceutical composition as hereinbefore defined to a subject.

No unacceptable toxicological effects are expected when compounds of the invention are administered in accordance with the present invention:

The biological activity of the compounds of Formula I are demonstrated by the following tests.

Induction of Colony Stimulating Activity by Stromal Cells

The murine bone marrow stromal cell line, C6, is grown to confluency in plastic tissue culture dishes in RPMI-1640 medium and 5% FBS. On the day prior to the experiment this medium is changed to DMEM without added serum. To these cultures, the compounds are added for one hour, then washed from the cultures. The medium is replaced with fresh DMEM and the cells are incubated for 24 hours at 37° C., 5% $CO_2$. After 24 hours the C6 cell culture supernatant is collected, sterile filtered, and frozen until it can be assayed for the presence of hematopoietic colony stimulating activity (CSA) as set forth below.

Soft Agar Assay

Bone marrow cells are obtained from Lewis rats. They are adjusted to $10^6$ cells/ml in DMEM without serum. A single layer agar system utilizing the following is used: DMEM enriched with nutrients ($NaHCO_3$, pyruvate, amino acids, vitamins, and HEPES buffer); 0.3% Bacto agar, and 20% Lewis rat serum. To this are added dilutions of C6 cell line supernatant (10–2.5%) from above along with rat bone marrow cells (final concentration=$10^5$ cells/ml). The agar plates are incubated at 37° C., 5% $CO_2$ for 7–8 days. Colonies of proliferating bone marrow cells (CFU-C) are counted utilizing a microscope. The number of agar colonies counted is proportional to the amount of CSA present within the C6 bone marrow stromal cell line supernatant.

Herpes Simplex Mouse Model

Seven days prior to infection, Balb/c mice are injected intraperitoneally once a day with a 0.2 ml volume at doses of 10 and 1 ng/kg of compound. Control mice receive injections of 0.1 ml of a mixture of the dilution buffer, DPBS and 0.5% heat inactivated normal mouse serum.

The mice are infected with a Herpes Simplex virus (strain MS) by injecting $5.0 \times 10^5$/pfu suspended in 0.05 mls of PBS in each rear foot pad. The mice continue to get compound or control injections until moribund (unable to get food or water). Usually paralysis of the hind leg occurs approximately eight days after infection. The paralysis progresses until encephalitis occurs.

Alternatively, the virus is inoculated by means of a vaginal route. A cotton plug containing $5.0 \times 10^5$/pfu of the MS-NAP strain is inserted into the vagina of the mouse.

A Wilcoxin test is used to determine if a significant increase in survival is found in the treated verses control group.

Candida challenge

Candida albicans strain B311a is used. This strain has been mouse passed then frozen at $-70°$ C. B311a is virulent to immunosuppressed mice in the range of 5.0 to $8.0 \times 10^4$ cfu/mouse and for normal mice in the range of 1.0 to $2.0 \times 10^5$ cfu/mouse. A sample from the frozen stock of Candida was grown on Sabouroud dextrose slants and then transferred to 50 ml. shake cultures of Sabouroud broth for 18 hours. The cells were washed three times, then counted by hemocytometer, and viability was confirmed by methylene dye exclusion. Viability counts were performed on the inoculum to confirm the counts.

All mice (Balb/c) infected with Candida were infected i.v. with cells suspended in 0.2 mls. of saline. Some mice are sublethally myelodepressed with 300 rads of irradiation. Beginning 2 hours following irradiation, the animals are injected with compound CSF as a positive control, or excipient, daily. Seven days after irradiation and treatment begins, the mice are challenged with Candida albicans by intravenous administration. Note that this represents approximately a LD75 for normal mice. In other studies the mice are not immunosuppressed. In these studies the mice are treated starting seven days post infection in the same manner as the irradiated mice. In both models the mice are followed until moribund and the change is survival compared using the Wilcoxin test.

The examples which follow serve to illustrate this invention. The examples are intended to in no way limit the scope of this invention, but are provided to show how to make and use the compounds of this invention.

In the examples, all temperatures are in degrees Centigrade. FAB mass spectra were performed upon a VG ZAB mass spectrometer using fast atom bombardment.

EXAMPLE 1

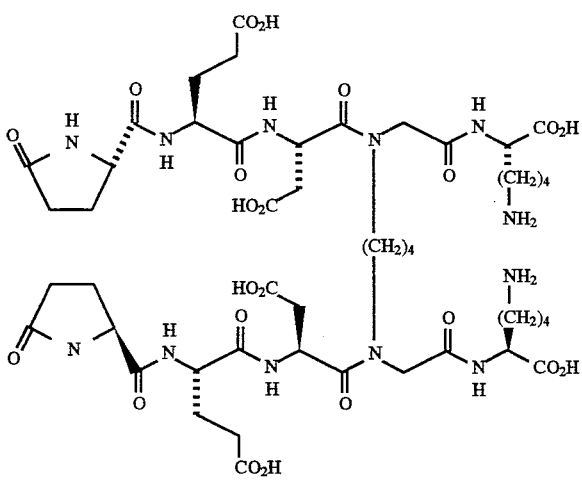

a) N,N'-Bis(methylcarboxyethoxy)-1,4-diaminobutane

A mixture of ethyl bromoacetate (2.40 mL, 21.6 mmol), Et$_3$N (4.20 mL, 30.1 mmol) and 1,4-diaminobutane (1.00 mL, 9.95 mmol) in CH$_2$Cl$_2$ (40 mL) was stirred at room temperature. After 2 h, the reaction mixture was poured into brine (100 mL) and extracted with CH$_2$Cl$_2$ (3×100 mL). The combined organic layers were dried over Na$_2$SO$_4$ and concentrated to give a white oil (1.53 g). Flash chromatography (10% MeOH/CHCl$_3$+1% Et$_3$N, silica gel) gave the desired compound as a yellow oil (0.57 g, 22%). $^1$H NMR (90 MH$_2$, CDCl$_3$) ∊4.25 (q, J=6.8 Hz, 4H), 3.40 (s,4H), 2.65 (m,4H), 1.65 (m,6H), 1.30 (t, J=6.8 Hz, 6H).

b) N,N',N,N'-Bis(t-butoxycarbonyl)bis(methylcarboxyethoxy)-1,4-diaminobutane

To a solution of (a) (0.57 g, 2.19 mmol) and Et$_3$N (1.25 mL, 8.97 mmol) in CH$_2$Cl$_2$ (20 mL) was added di-t-butyl dicarbonate (1.44 g, 6.60 mmol). After 18 h, the reaction was poured into brine (50 mL) and extracted with CH$_2$Cl$_2$ (3×75 mL). The combined organic extracts were dried over Na$_2$SO$_4$ and concentrated to give an off-white residue (1.50 g). Flash chromatography (30% EtOAc/hexane, silica gel) gave the desired product as a clear oil (0.89 g, 88%). MS (ES+) m/e 461.2 [M+H]$^+$ c)

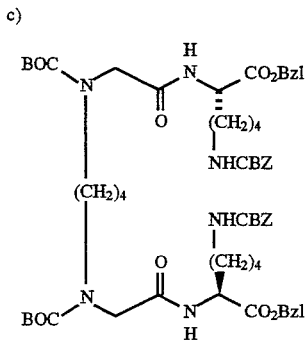

A mixture of (b) (0.37 g, 0.80 mmol) in THF (5 mL) and 1N NaOH (5 mL, 5 mmol) was stirred at room temperature. After 18 h, the reaction was diluted with CHCl$_3$ (20 mL) and acidified with 1N HCl. The aqueous layer was further extracted with CHCl$_3$ (2×20 mL). The combined organic layers were washed with brine (25 mL), dried over Na$_2$SO$_4$ and concentrated to give a clear oil (0.29 g). This material solidified on standing and was used without further purification in the next step.

To Lys (CBZ)OBzl.HCl (0.72 g, 1.77 mmol) in DMF (3 mL) at −10° C. was added EtNiPr$_2$ (0.31 mL, 1.76 mmol) and HOBt (0.25 g, 1.82 mmol). To the resulting solution was added a solution of the diacid (0.29 g, 0.80 mmol) obtained above in DMF (3 mL) followed by EDC (0.34 g, 1.77 mmol). The reaction was allowed to warm to room temperature. After 18 h, the reaction was poured into 5% Na$_2$CO$_3$ in brine (200 mL) and extracted with CHCl$_3$ (4×50 mL). The combined organic portions were washed with H$_2$O (50 mL), 1N HCl (2×50 mL), brine (2×50 mL), dried over MgSO$_4$ and concentrated to give an orange oil. Flash chromatography (2.5% MeOH, CHCl$_3$, silica gel) gave the desired compound as a white solid (0.67 g, 75%). MS (ES+) m/e 1109.6 [M+H]$^+$ d)

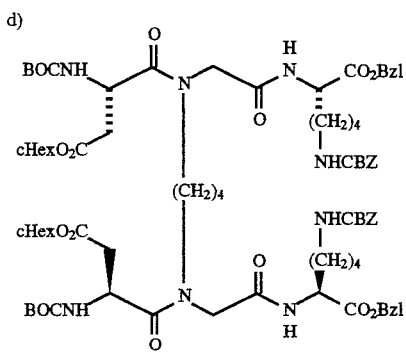

To a solution of (c) (0.11 g, 0.10 mmol) in CH$_2$Cl$_2$ (2 mL) was added TFA (2 mL). After 1 h at room temperature, the solvent was removed in vacuo. The resulting orange oil was azeotroped with toluene, dissolved in DMF (0.5 mL) and added to neat Boc-Asp(OcHex) (0.14 g, 0.44 mmol) and HOBt (0.06 g, 0.44 mmol). To the resulting solution was added EtNiPr$_2$ (0.8 mL, 0.44 mmol) and EDC (0.08 g, 0.43 mmol). After 18 h, the reaction was poured into 5% Na$_2$CO$_3$ in brine (200 mL and extracted) with CHCl$_3$ (4×50 mL). The combined organic portions were washed in H$_2$O (50 mL), 1N HCl (2×50 mL), brine (2×50 mL), dried over MgSO$_4$ and concentrated to give a waxy solid. Flash chromatography (1% MeOH/CHCl$_3$, silica gel) gave the desired compound (0.08 g, 51%). MS (ES+) m/e 1503.8 [M+H]$^+$.

e)

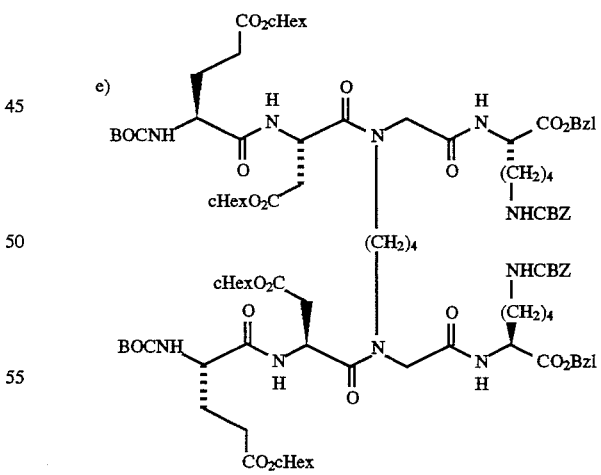

To a solution of (d) (0.08 g, 50.0 µmol) in CH$_2$Cl$_2$ (5 mL) was added TFA (5 mL). After 1 h at room temperature, the solvent was removed in vacuo. The resulting oil was azeotroped with toluene, dissolved in DMF (0.5 mL) and added to neat Boc-Glu(OeHex) (76.3 mg, 0.22 mmol) and HOBt (31.1 mg, 0.23 mmol). To the resulting solution was added EtNiPr$_2$ (38.0 µL, 0.22 mmol) and EDC (45.6 mg, 0.24 mmol). After 18 h, the reaction was poured into 5% Na$_2$CO$_3$ in brine (200 mL) and extracted with CHCl₃ (4×50 mL). The combined organic portions were washed in H₂O (50 mL), 1N HCl (2×50 mL), brine (2×50 mL), dried over MgSO₄ and concentrated to give a white solid. Flash chromatography (5% MeOH/CHCl₃, silica gel) gave the desired compound (31.0 mg, 30%). MS (ES+) m/e 963.6 [M+H]$^{2+}$.

f)

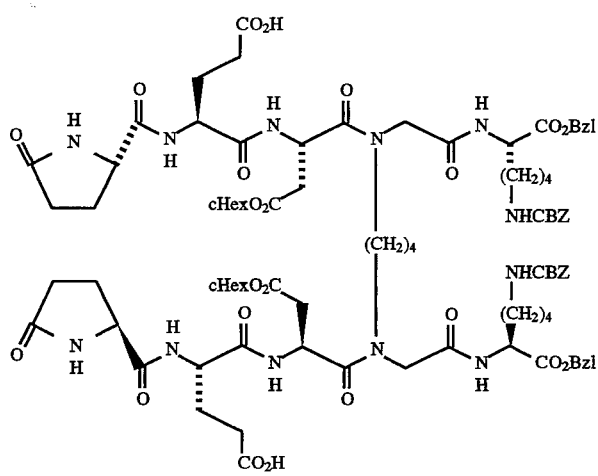

To a solution of (e) (30 mg, 15.6 μmol) in CH₂Cl₂ (2 mL) was added TFA (52 mL). After 1 h at room temperature, the solvent was removed in vacuo. The resulting oil was azeotroped with toluene, dissolved in DMF (0.5 mL) and added to neat pGlu (12.8 mg, 99.1 μmol) and HOBt (10.1 mg, 74.5 μmol). To the resulting solution was added EtNiPr₂ (12.0 μL, 68.9 μmol) and EDC (13.8 mg, 72.1 μmol). After 18 h, the reaction was poured into 1:1 ice/water (100 mL). The resulting precipitate was collected and dried under vacuum to give a white solid (15.9 mg, 52%). MS (ES+) m/e 975.0 [M+2H]$^{2+}$ g) Compound 1

An HF vessel at −78° C. was charged with (f) (14.9 mg, 7.6 μmol), anhydrous HF (5 mL) and p-cresol (0.5 mL). The reaction was warmed at 0° C. After 1.5 h at 0° C., the HF was removed in vacuo and the residue was dissolved in 4% aqueous acetic acid. This material was lyophilized to dryness. Preparative HPLC (Vydac™ C-18, 2.5% to 50% acetonitrile/water+0.1% TFA over 60 min) gave the title compound as a white solid. MS (FAB) m/e 1171.4 [M+H]⁺.

EXAMPLE 2

Formulations for pharmaceutical use incorporating compounds of the present invention can be prepared in various forms and with numerous excipients. Examples of such formulations are given below.

|  | Tablets/Ingredients Per Tablet |
| --- | --- |
| 1. Active ingredient (Cpd of Formula I) | 0.5 mg |
| 2. Corn Starch | 20 mg |
| 3. Alginic acid | 20 mg |
| 4. Sodium alginate | 20 mg |
| 5. Mg stearate | 1.3 mg |

Procedure for tablets:

Step 1 Blend ingredients No. 1, No. 2, No. 3 and No. 4 in a suitable mixer/blender.

Step 2 Add sufficient water portion-wise to the blend from Step 1 with careful mixing after each addition. Such additions of water and mixing until the mass is of a consistency to permit its conversion to wet granules.

Step 3 The wet mass is converted to granules by passing it through an oscillating granulator using a No. 8 mesh (2.38 mm) screen.

Step 4 The wet granules are then dried in an oven at 140° F. (60° C.) until dry.

Step 5 The dry granules are lubricated with ingredient No. 5

Step 6 The lubricated granules are compressed on a suitable tablet press.

Parenteral Formulation

A pharmaceutical composition for parenteral administration is prepared by dissolving an appropriate amount of a compound of formula I in polyethylene glycol with heating. This solution is then diluted with water for injections Ph Eur. (to 100 ml). The solution is then sterilized by filtration through a 0.22 micron membrane filter and sealed in sterile containers.

What is claimed is:

1. A compound of the following formula:

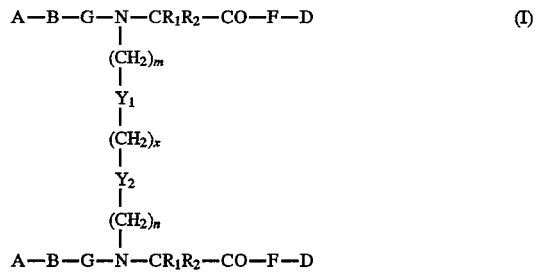

wherein:

Y₁ and Y₂ are independently CH₂ or S;

x is 0, 1, 2, 3, or 4;

m is 0 or 2;

n is 0 or 2;

A is pyroglutamic acid, proline, glutamine, tyrosine, glutamic acid, 2-thiophene carboxylic acid, picolinic acid, cyclohexane carboxylic acid, tetrahydro-2-furoic acid, tetrahydro-3-furoic acid, 2-oxo-4-thiazolidine carboxylic acid, cyclopentane carboxylic acid, 3-thiophene carboxylic acid, (S)-(+)-5-oxo-2-tetrahydrofuran carboxylic acid, pipecolinic acid, pyrrole carboxylic acid, isopyrrole carboxylic acid, pyrazole carboxylic acid, isoimidazole carboxylic acid, triazole carboxylic acid, dithiole carboxylic acid, oxathiole carboxylic acid, isoxazole carboxylic acid, oxazole carboxylic acid, thiazole carboxylic acid, isothiazole carboxylic acid, oxadiazole carboxylic acid, oxatriazole carboxylic acid, oxathiolene carboxylic acid, oxazine carboxylic acid, oxathiazole carboxylic acid, dioxazole carboxylic acid, pyran carboxylic acid, pyrimidine carboxylic acid, pyridine carboxylic acid, pyridazine carboxylic acid, pyrazine carboxylic acid, piperazine carboxylic acid, triazine carboxylic acid, isooxazine carboxylic acid, oxathiazene carboxylic acid, morpholine carboxylic acid, indole carboxylic acid, indolenene carboxylic acid, 2-isobenzazole carboxylic acid, nicotinic acid, isonicotinic acid, pyrazolo [3,4-b]pyrrole carboxylic acid, pyrazolo [3,4-b]pyrrole carboxylic acid, isoindazole carboxylic acid, indoxazine carboxylic acid, benzoxazole carboxylic acid, anthranil carboxylic acid, quinoline carboxylic acid, isoquinoline carboxylic acid, cinnoline carboxylic acid, quinazolene carboxylic acid, naphthyridine carboxylic acid, pyrido[3,4-b]-pyridine carboxylic acid, pyrido[3,2-b]-pyridine carboxylic acid, pyrido[4,3-b]pyridine carboxylic acid, 1,3,2-benzoxazine carboxylic acid, 1,4,2-benzoxazine carboxylic acid, 2,3,1-benzoxazine carboxylic acid, 3,1,4-benzoxazine carboxylic acid, 1,2-benzisoxazine carboxylic acid, 1,4-benzisoxazine carboxylic acid, carbazole carboxylic acid, acridine carboxylic acid, or purine carboxylic acid;

B is serine, threonine, glutamic acid, tyrosine, cysteine or aspartic acid;

G is glutamic acid, tyrosine, aspartic acid, serine, alanine, phenylalanine, histidine, isoleucine, leucine, methionine, threonine, trytophan, norleucine, allothreonine, glutamine, asparagine, valine, proline, glycine, lycine, β-alanine or sarcosine;

D is lysine, arginine, tyrosine, N-methyl-arginine, aspartic acid, ornithine, serine, alanine, phenylalanine, histidine, isoleucine, leucine, methionine, threonine, trytophan, norleucine, allothreonine, glutamine, asparagine, valine, proline, glycine, lysine, β-alanine, sarcosine, or diaminohexynoic acid; or the carboxyamide, or the hydroxy methyl or N-methyl derivative thereof;

F is tyrosine or a peptide bond;

$R_1$ and $R_2$ are independently hydrogen, $C_{1-3}$alkyl, $C_{2-4}$alkenyl, $C_{2-4}$alkynyl, $(CH_2)_n Ar$ or $(CH_2)_x R_3$;

$R_3$ is OH, SH, $NH_2$, —NH C($NH_2$)NH, $CO_2H$ or $CONH_2$;

Ar is phenyl, pyridyl, furyl, naphthyl, thiophenyl, pyrrolyl, imidazolyl, indolyl or hydroxyphenyl;

Provided that:

when $Y_1$ and $Y_2$ are S, x is 0, 2, 3 or 4 and m and n are 2; or when $Y_1$ and $Y_2$ are $CH_2$, x is 0, 1, 2, 3 or 4 and m and n are 0; or when $Y_1$ is S and $Y_2$ is $CH_2$, x is 0, m and n are;

or a pharmaceutically acceptable salt thereof.

2. A compound according to claim 1 wherein A is pyroglutamic acid, picolinic acid, proline, or pipecolenic acid.

3. A compound according to claim 2 wherein B is glutamic acid, serine, aspartic acid or tyrosine.

4. A compound according to claim 3 wherein G is aspartic acid, glutamic acid, tyrosine or lysine and D is lysine or the carboxyamide derivative thereof, arginine, N-methylarginine, 2,6-diamino-4-hexanoic acid, aspartic acid or ornithine.

5. A pharmaceutical composition comprising a compound of claim 1 and a pharmaceutically acceptable carrier.

6. A method of stimulating the myelopoietic system which comprises administering to a subject in need thereof, an effective amount of a compound according to claim 1.

7. A method of treating viral, fungal and bacterial infections which comprises administering to a subject in need thereof, an effective amount of a compound of claim 1.

8. A method of treating Candida or Herpes or Hepatitis infections which comprises administering to a subject in need thereof, an effective amount of a compound of claim 1.

\* \* \* \* \*